United States Patent [19]

Louderback

[11] Patent Number: 4,833,165

[45] Date of Patent: May 23, 1989

[54] METHOD OF INACTIVATING HTLV-III VIRUS IN BLOOD

[76] Inventor: Allan L. Louderback, 9661 Longden Ave., Temple City, Calif. 91780

[21] Appl. No.: 105,340

[22] Filed: Oct. 7, 1987

[51] Int. Cl.⁴ .................... A61K 31/115; A61K 31/05
[52] U.S. Cl. .................................. 514/694; 514/696; 514/731; 422/28; 422/36
[58] Field of Search ............... 514/694, 696, 731, 934; 422/28, 31, 36

[56] References Cited

U.S. PATENT DOCUMENTS 3,973,913  8/1976  Louderback ......................... 436/11
4,675,159  6/1987  Al-Sioufi .............................. 422/36

OTHER PUBLICATIONS

Remington's Pharmaceutical Sciences, 16th Ed., 1980, pp. 1110, 1262–1263 and 1329–1330.
American Hospital Formulary Service 86, pp. 1697–1703.
AMA Drug Evaluations, 5th Ed., 1983, pp. 1399, 1404, 1411 and 1413.
The Merck Index, 10th Ed., 1983, cite #4120 and 7115.

*Primary Examiner*—Douglas W. Robinson
*Assistant Examiner*—Raymond J. Henley, III
*Attorney, Agent, or Firm*—Eric P. Schellin

[57] ABSTRACT

HTLV-III virus in blood or blood components is inactivated by treatment with about 0.1–5% of phenol, formaldehyde, or mixtures thereof, at a temperature of about 2°–40° C. for at least about 5 minutes.

5 Claims, No Drawings

METHOD OF INACTIVATING HTLV-III VIRUS IN BLOOD

BACKGROUND OF THE INVENTION

This invention relates to a method of inactivating HTLV-III virus in blood and blood components.

In recent years, considerable effort has been undertaken by scientists and blood bank specialists to free the nation's blood supply from contamination by viruses, especially the hepatitis viruses. Various approaches have been used, including separation of the viruses by adsorption, filtration and other such physical methods of separation. Chemical treatment to inactivate the viruses also has been used either by itself or in combination with physical separation methods. Thus, use of β-propionolactone with colloidal silica adsorption is described in U.S. Pat. No. 4,370,264. Treatment with a wide variety of surfactants is described in many patents, for example, U.S. Pat. Nos. 4,314,997; 4,315,919; 4,481,189; 4,591,505; and 4,613,501. Treatment with other organic liquids such as halohydrocarbons is taught in U.S. Pat. No. 4,511,556, and various alkanes, ketones and perfluorocarbons are suggested in U.S. Pat. No. 4,490,361. Use of ion exchange resins is disclosed in U.S. Pat. No. 4,590,002. Still another approach involves heat treatment of the blood or blood component to inactivate the viruses. This is illustrated, for example, in U.S. Pat. No. 4,495,278.

With the recent discovery and identification of the virus reported to cause acquired immune deficiency syndrome (AIDS), an additional contamination problem has appeared with respect to the blood supply. This contamination can arise through collection of blood from donors carrying the AIDS virus. This retrovirus, the third known T-lymphocyte virus (HTLV-III), has the capacity to replicate within cells of the immune system and thereby lead to a profound destruction of T4+T cells. See Gallo et al., *Science* 224, 500–503 (1984), and Popovic et al., Ibid., 497–500 (1984). The virus has also been called lymphadenopathy-associated virus (LAV) or AIDS-associated retrovirus (ARV) and, more recently, human immunodeficiency virus (HIV).

While suggestions have been made for individuals to avoid the potential problem of blood contamination with the AIDS virus by making autologous blood donations, such approaches are not likely to be practical except for storing relatively small amounts of blood for scheduled operations.

Accordingly, a method for inactivating or removing the AIDS virus from stored blood and blood components would have significant utility.

BRIEF DESCRIPTION OF THE INVENTION

In accordance with the present invention a method is provided for inactivating HTLV-III virus in blood and blood components. The method comprises treating the blood or blood component with an effective amount of from about 0.1% to about 5% of a chemical agent which can be phenol, formaldehyde, or mixtures thereof, at a temperature of from about 2° C. to about 40° C. for at least about 5 minutes, preferably from about 30 to about 60 minutes, and then thoroughly washing the residual chemical agent from the thus-treated blood or blood component.

Although phenol and formaldehyde have been widely used heretofore as antiseptic, preservative and antimicrobial agents in vaccines, pharmaceuticals and other biological preparations, they are not believed to have been known to inactivate the HTLV-III virus as defined according to the present invention.

The absence of the HTLV-III virus from the blood or blood components treated by the method of the present invention has been confirmed by use of the U.S. Food and Drug Administration (FDA) approved AIDS immunoassay, namely the ELISA test described in Gallo, U.S. Pat. No. 4,520,113. This patent has been licensed by the U.S. Government to several U.S. companies, including Abbott Laboratories. Another suitable test is the so-called Western Blot test which has recently been licensed by the FDA to Biotech Research Laboratories, Inc., and DuPont Co.

DETAILED DESCRIPTION OF THE INVENTION

In accordance with a preferred method of the invention, the HTLV-III virus is inactivated by treatment of the red blood cell component of blood that has been contaminated with the virus. For such treatment of the red blood cells, the cells can be separated from whole blood and washed with phenol, formaldehyde, or mixtures thereof, by a washing procedure essentially as described in U.S. Pat. No. 3,973,913, by employing said chemical agents in an intermediate washing step as described therein with formaldehyde. By this preferred method, the treatment of the red blood cells with phenol, formaldehyde, or mixtures thereof, is combined with a washing step to physically partition the inactivated virus from the red blood cells.

According to this preferred method of the invention, the red blood cells are first sedimented or centrifuged and thoroughly washed to ensure complete separation from the other blood components. Following this separation, the cells are resuspended and then treated with the phenol, formaldehyde, or mixtures thereof, to inactivate the HTLV-III virus. After said treatment, the cells are again washed thoroughly to remove the residual chemical agent. The cells are then resuspended and stored or retained for use in administration as needed.

In the washing process, after each unit (e.g., one liter) of washing solution is washed into the cells in the centrifuge bowl, the centrifuge is stopped for about 2 to 5 minutes to allow the cells at the sides of the bowl to swirl into and be mixed well with the solution. The centrifuge is then restarted to push the well-mixed and washed cells back to the sides of the bowl. Then the next unit of wash solution is fed into the system and the wash cycle is repeated.

Sedimentation and washing is facilitated by spinning in a conventional blood centrifuge. Centrifuge for such blood cell sedimentation are well-known, and a continuous flow type centrifuge such as is commercially available from Haemonetics Corp. is preferred. Centrifuges of this type are described, for example, in U.S. Pat. No. 3,706,412. In this type of centrifuge, the bowl has two parts, one that rotates and another that is stationary. As the blood or previously separated red blood cells enter the spinning bowl, the cells are distributed to the periphery and as the bowl fills, the supernatant separates from the red blood cells. The red blood cells are held in suspension by centrifugal force while the supernatant is expelled through an effluent port into a waste collection receptacle.

The washing solution is made to follow the same path as the red blood cells. The washing solution is a saline solution which preferably is normal physiological saline containing about 0.9% NaCl but can also contain other substances such as, for example, anticoagulant components acceptable for human blood transfusions, e.g., ACD (acid, citrate, dextrose), CPD (citrate, phosphate, dextrose), CPD-A (CPD+adenine), and various types of blood rejuvenant solutions. The geometry of the centrifuge keeps the cells circulating against the flow of fresh wash solution as the used wash solution is expelled through the effluent port. After the final washing step, the centrifuge is stopped and the washed cells are siphoned into a separate collection vessel.

In the foregoing washing procedures, the red blood cells are preferably washed with a total of from about 2 to about 30 volumes of the saline washing solution. In a preferred example, a unit of blood (375 ml.) is washed with about 3-4 liters of saline. Preferably, two washes with saline (one liter each wash cycle) and two washes with ACD solution (one liter each wash cycle) are employed in the initial washing step.

Following the saline and ACD washing, the red blood cells are ready for the treatment with phenol, formaldehyde, or mixtures thereof. If not treated immediately, it is preferred to temporarily store the cells in acceptable anticoagulant solution, e.g., ACD solution. This solution can be prepared by admixing the following components in the stated amounts and diluting with water to a volume of one liter:

| Component | Amount |
| --- | --- |
| Tri-sodium citrate | 8.0 gm |
| Citric acid | 150.0 mg |
| Dextrose | 20.0 gm |

The components of ACD solution should be mixed well and the pH adjusted to within a range of from about 6.4 to about 6.8. The washed red blood cells can be retained in the ACD solution for about 45 days at 20° C. to 8° C.

The washed red blood cells, when ready for the chemical agent treatment, are first resuspended in saline solution in proportions of about one volume of cells to about 5 to 30 parts by volume of the saline. The cells are mixed with the phenol, formaldehyde, or mixtures thereof, at a temperature of from about 2° C. to about 40° C. The chemical agent concentration during the mixing preferably ranges from about 0.1% to about 5%. The mixing of the cells and the chemical agent solution should be maintained for at least about 5 minutes, and preferably from about 30 minutes to 60 minutes.

Following the treatment with phenol, formaldehyde, or mixtures thereof, the thus treated cells are sedimented such as by centrifugation and again washed with saline in about the same range of proportions as in the initial saline washing.

As before, the red blood cells can be used directly for administration or stored temporarily in ACD solution at 2° C. to 8° C.

The following detailed examples will further illustrate the invention although it will be understood that the invention is not limited to these specific examples.

EXAMPLE 1

Illustrative formulations of the chemical agent treatment solutions for inactivating the HTLV-III virus are prepared as follows:

Formaldehyde—40 ml. of a 37% solution of formaldehyde are mixed with 500 ml of saline. This is equivalent (40/540) to 7.4 ml per 100 ml×37%, or a 2.7% solution of HCHO.

Phenol—12.5 grams of phenol are mixed with 500 ml of saline. This is equivalent (12.5/500) to 2.5 grams per 100 ml, or a 2.5% solution of phenol.

Phenol/Formaldehyde Mixture—250 ml of each of the above solutions of phenol and formaldehyde are mixed to give 500 ml of a 2.6% solution of the mixture.

These chemical agent solutions can then be used directly for treatment of the blood or blood component, e.g., washed red blood cells, as described in the following examples.

EXAMPLE 2

Outdated blood packs were initially obtained from the American Red Cross. For each test or run as follows, blood of only a single blood type was used. The blood was washed into a Haemonetics centrifuge bowl (volume 375 ml) by adding 200 ml of saline (0.9% NaCl) to the bag mixing and then allowing the blood to flow by gravity into the spinning bowl system. After all the blood was in the bowl, the cells were washed with 2 liters of sterile saline and 2 liters of ACD solution in consecutive washing cycles of one liter each, to remove the plasma from the cells. The washed red blood cells were collected in a clean container for treatment with formaldehyde in the viral inactivating tests below. The washed red blood cells were stored temporarily in ACD solution at 5° C. before undergoing the formaldehyde treatment.

The viral inactivating tests were initiated by adding 0.4 ml of HTLV-III virus concentrate (containing 4-5 logs of virus per ml, or 10,000–100,000 infectious doses of virus per ml) to each of two 4.4 ml samples of the above washed red blood cells in separate tubes. The virus was thus made to comprise 1/11 of each sample. One sample (designated ACT) was then subjected to the formaldehyde treatment to inactivate the virus while the other sample (designated CCC) was untreated to serve as a control as follows:

HCHO treated sample (ACT)—1000 μl of formaldehyde treatment solution (2.7% HCHO) was added to the virally contaminated cells in this tube and the material gently stirred for 40 minutes.

Control sample (CCC)—The virally contaminated cells in this tube were untreated but gently stirred for 40 minutes as the treated sample, above.

Cells were then pipetted from the above sample tubes in 1 ml volume amounts into each of four small plastic centrifuge tubes. These tubes, that is, 4 tubes for each of the above control (CCC) and HCHO treated (ACT) samples, were centrifuged to spin down the cells. Then 1.1 ml of saline (0.9% NaCl) was added to each tube to resuspend the cells and mix them. The supernatant solution from this first wash was emptied into Clorox ® (sodium hypochlorite) solution to decontaminate it.

The cells were then washed 2 more times in saline (1.1 ml each time), followed by 2 washes in commercially available RPMI-1640 tissue culture medium. With each washing, the supernatant was discarded into the Clorox decontamination solution to prevent the accidental spread of virus.

During the above treatment period, no lysis or breakdown of red blood cells has occurred.

The thus treated cells in each tube were pooled into a final amount in their respective tubes (control and formaldehyde treated) and diluted with 2.2 ml of the RPMI-1640 tissue culture medium.

Next, a ½ dilution was made of each tube. Then the cells were serially diluted 1:10 for 4 more tubes to provide the following virus dilutions for both cell samples (control and formaldehyde treated), with the respective tubes labeled as follows:

| T.S. | A | B | C | D | E |
|---|---|---|---|---|---|
| 1/11 | 1/22 | 1/220 | 1/2200 | 1/22,000 | 1/220,000 |

Thus, the assay dilutions (HIV=HTLV-III virus) were as follows:

| Assay Tube | Description | Total Virus Dilution |
|---|---|---|
| Test Sample | 1/11 of HIV in test sample | 1:11 of HIV |
| A | 1:2 of test sample | 1:22 of HIV |
| B | 1:10 of A | 1:220 of HIV |
| C | 1:10 of B | 1:2200 of HIV |
| D | 1:10 of C | 1:22,000 of HIV |
| E | 1:10 of D | 1:220,000 of HIV |

In this test procedure, 1.5 ml of each sample was added to 24 well microtiter plates. Then H-9 tissue culture medium was seeded at a density of $10^5$ cells per well. The samples were incubated for 10 days at 37° C. in an atmosphere of 95% oxygen and 5% carbon dioxide. The tissue medium overlaying the red blood cells was changed with fresh medium on days 3, 7 and 10. H-9 cells are transformed human lymphocytes.

Each of the above tubes was held at 5° C. until inoculated into the H-9 tissue culture. Every step was carried out aseptically to prevent any adventitious contamination. By this test procedure, if virus is present in the test sample, it will grow in the tissue culture. That is, if the red blood cells are infected with the HTLV-III virus, the virus will grow in the medium during the incubation period and the resulting HTLV-III antigens can then be assayed.

0.2 ml samples of the supernatant fluid from the microtiter plates were taken up on day 10 and assayed for the presence of HTLV-III/LAV/HIV p24 antigen by an enzyme-linked immunosorbent assay (ELISA) test. The results are expressed as reactive (positive, +) or non-reactive (negative, −) for each well. The test samples were compared to a known negative and a known positive sample grown at the same time in the same system as above.

The results after the 10 days were as follows:

| | Tube | | | | |
|---|---|---|---|---|---|
| | A 1/22 | B 1/220 | C 1/2200 | D 1/22,000 | E 1/220,000 |
| CCC | + | + | + | − | − |
| ACT | − | − | − | − | − |

It is thus seen from the above that on the 10th day the control samples did not become negative until a dilution of 1/22,000 (Tube D) whereas the formaldehyde treated samples were negative at 1/22 dilution. This constitutes a loss of activity of 3.34 log units of virus by the formaldehyde treatment. Thus, the treated red blood cell samples were free of virus whereas the untreated cells were extremely infective.

EXAMPLE 3

Chemical agent treatment solutions for inactivating HTLV-III virus in washed red blood cells were prepared in saline solution in concentration as follows:

| Formaldehyde | Solution A - 1.39% in saline |
|---|---|
| | Solution B - 0.69% in saline |
| Phenol | Solution C - 1.29% in saline |
| | Solution D - 0.64% in saline |
| 1:1 Mixture of Phenol/Formaldehyde | Solution E - 0.67% in saline |

These chemical agent solutions were used to treat washed red blood cells essentially as in Example 2, which were exogenously contaminated with HTLV-III virus at 11,500 virus infectious doses per ml as determined by ELISA testing. Upon treatment with the above chemical agent solutions and again testing by ELISA, no virus was found in any of the treated cells or supernatant fluid after the 30 minute treatment period.

Various other examples will be apparent to the person skilled in the art after reading the present disclosure without departing from the spirit and scope of the invention. It is intended that all such other examples be included within the scope of the appended claims.

What is claimed is:

1. A method of inactivating HTLV-III virus in blood collected for administration to a human being in need of said blood which comprising the steps of:
   separating red blood cells from whole blood contaminated by said virus washing said red blood cells in a saline solution, resuspending said red blood cells in a saline solution;
   treating said red blood cells with an effective amount of from about 0.1% to about 5% by weight of said resuspended red blood cell and saline solution of a chemical agent selected from the group consisting of phenol, formaldehyde and mixtures thereof at a temperature of from about 2° C. to about 40° C. for at least about 5 minutes; and thoroughly washing the residual chemical agent from the thus treated red blood cells with a saline solution.

2. A method of claim 1 in which the red blood cells are resuspended in a saline solution in proportions of about one volume of cells to about 5 to 30 parts by volume of saline.

3. The method of claim 1 in which the treatment time with the chemical agent ranges from about 30 minutes to about 60 minutes.

4. The method of claim 1 in which the chemical agent is formaldehyde.

5. The method of claim 1 in which the chemical agent is phenol.

* * * * *